(12) United States Patent
Liu et al.

(10) Patent No.: US 11,110,444 B2
(45) Date of Patent: Sep. 7, 2021

(54) CHIRAL CATALYST AND HETEROGENEOUS CHIRAL CATALYST COMPRISING THE SAME

(71) Applicant: INDUSTRIAL TECHNOLOGY RESEARCH INSTITUTE, Hsinchu (TW)

(72) Inventors: Shih-Hsien Liu, Jhubei (TW); Yi-Liang Tsai, Taichung (TW); Chih-Lung Chin, Hsinchu (TW); Chien-Wen Lin, Taoyuan (TW); Chao-Wu Liaw, Yunlin County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 95 days.

(21) Appl. No.: 16/730,345

(22) Filed: Dec. 30, 2019

(65) Prior Publication Data
US 2021/0197182 A1    Jul. 1, 2021

(51) Int. Cl.
| | | |
|---|---|---|
| *B01J 31/26* | (2006.01) | |
| *B01J 31/02* | (2006.01) | |
| *B01J 21/08* | (2006.01) | |
| *B01J 35/10* | (2006.01) | |
| *C07D 401/14* | (2006.01) | |

(52) U.S. Cl.
CPC .......... *B01J 31/0274* (2013.01); *B01J 21/08* (2013.01); *B01J 31/26* (2013.01); *B01J 35/1014* (2013.01); *B01J 35/1019* (2013.01); *B01J 35/1023* (2013.01); *B01J 35/1061* (2013.01); *C07D 401/14* (2013.01); *B01J 2231/643* (2013.01); *B01J 2531/002* (2013.01)

(58) Field of Classification Search
CPC .................................................... C07D 401/14
See application file for complete search history.

(56) References Cited

U.S. PATENT DOCUMENTS

| | | |
|---|---|---|
| 7,056,540 B2 | 6/2006 | Yadav et al. |
| 8,263,799 B2 | 9/2012 | Lin et al. |
| 8,449,953 B2 | 5/2013 | Cheng et al. |
| 8,540,896 B2 | 9/2013 | Chin et al. |
| 9,000,192 B2 * | 4/2015 | Yamada ............... B01J 31/0245 549/78 |
| 9,181,217 B2 | 11/2015 | Matsuyama et al. |
| 9,388,205 B2 | 7/2016 | Lee et al. |
| 10,189,760 B2 | 1/2019 | Hong et al. |
| 2008/0200672 A1 | 8/2008 | Ortiz-Marciales et al. |
| 2009/0163601 A1 | 6/2009 | Meyer et al. |
| 2017/0334823 A1 * | 11/2017 | Sankaranarayanapillai ................ C10L 1/04 |

FOREIGN PATENT DOCUMENTS

| | | |
|---|---|---|
| CN | 103819489 A | 5/2014 |
| CN | 109265385 A | 1/2019 |
| IN | 277664 | 5/2012 |
| TW | 201028374 A1 | 8/2010 |
| TW | I598432 B | 9/2017 |
| TW | I641589 B | 11/2018 |

OTHER PUBLICATIONS

Kim et al., Microporous and Mesoporous Materials, 523-529 (2001) (Year: 2001).*
T. Fang et al., 10 Synlett, 1559-1563 (2006) (Year: 2006).*
T. Fang et al., 7 Organic Letters, 2081-2084 (2005) (Year: 2005).*
S. Bae et al., Chemical Communications, 31-32 (2000) (Year: 2000).*
P. McMorn et al., 33 Chem. Soc. Rev., 108-122 (2004) (Year: 2004).*
M. Heitbaum et al., 45 Angew. Chem. Int. Ed., 4372-4762 (2006) (Year: 2006).*
A. Corma et al., 348 Adv. Synth. Catal., 1391-1412 (2006) (Year: 2006).*
T. Fang et al., 3 Letters in Organic Chemistry, 780-786 (2006) (Year: 2006).*
Dai et al., "Efficient Synthesis of (R)-Phenylophrine Using a Polymer-supported Corey-Bukshi-Shibata Catalyst", Chem. Lett., vol. 46, 2017, pp. 740-743 (5 pages).

(Continued)

*Primary Examiner* — Alexander R Pagano
(74) *Attorney, Agent, or Firm* — Birch, Stewart, Kolasch & Birch, LLP

(57) ABSTRACT

A chiral catalyst represented by formula (II) is provided. In formula (II), Y independently includes hydrogen, fluorine, trifluoromethyl, isopropyl, tert-butyl, $C_mH_{2m+1}$ or $OC_mH_{2m+1}$, wherein m=1-10 and n=1-10. A heterogeneous chiral catalyst is also provided. The heterogeneous chiral catalyst includes the chiral catalyst represented by formula (II), and a substrate connected to the chiral catalyst.

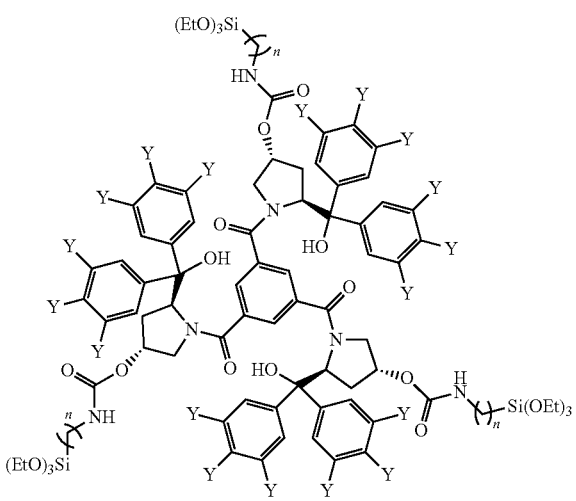

(II)

13 Claims, No Drawings

(56) References Cited

OTHER PUBLICATIONS

Du et al., "Structurally Well-Defined, Recoveralbe C₂-Symmetric Tris(β-hydroxy phosphoromide)-Catalyzed Enantioselective Borane Reduction of Ketones", Organic Letters, vol. 8, No. 7, 2006, pp. 1327-1330 (4 pages).
Kim et al., "Chiral proline-derivative anchored on mesoporous silicas and their application to the asymmetric diethylzinc addition to benzaldehyde", Microporous and Mesoporous Materials, vol. 44-45, 2001, pp. 523-529 (7 pages).
Padiya et al, "Fluoxetine: A Practical Approach Using Recyclable and it-situ Generated Oxazaborolidine Catalyst", Chinese Journal of Chemistry, vol. 27, 2009, pp. 1137-1140 (4 pages).
Thvedt et al., "Enantioselectivity, swelling and stability of 4-hydroxyprolinol containing acrylic polymer beads in the asymmetric reduction of ketones", Tetrahedron: Asymmetry, vol. 22, 2011, pp. 2172-2178 (7 pages).
Wang et al., "Diphenyfamine-derived bis-hydoxyamide catalyzed asymmetric borane reduction of prochiral ketones", Tetrahedron: Asymmetry, vol. 20, 2009, pp. 605-609 (5 pages).

\* cited by examiner

CHIRAL CATALYST AND HETEROGENEOUS CHIRAL CATALYST COMPRISING THE SAME

TECHNICAL FIELD

The present disclosure relates to a chiral catalyst for selective reduction of enantiomers, and a heterogeneous chiral catalyst including the chiral catalyst.

BACKGROUND

Chiral catalysts' intermolecular forces and steric hindrances can induce reactions to form left- or right-handed molecules. Generally speaking, the criteria for success in the application of chiral catalysts to asymmetric synthesis is that the products have high optical purity, that the chiral catalysts are recyclable, that both L- and D-isomers can be prepared separately, and that the products have a high conversion rate.

However, in a homogeneous reaction, the chiral catalyst will eventually be mixed with the target products, increasing the difficulty and cost of recovery of the catalysts.

SUMMARY

The present disclosure provides a chiral catalyst represented by formula (I):

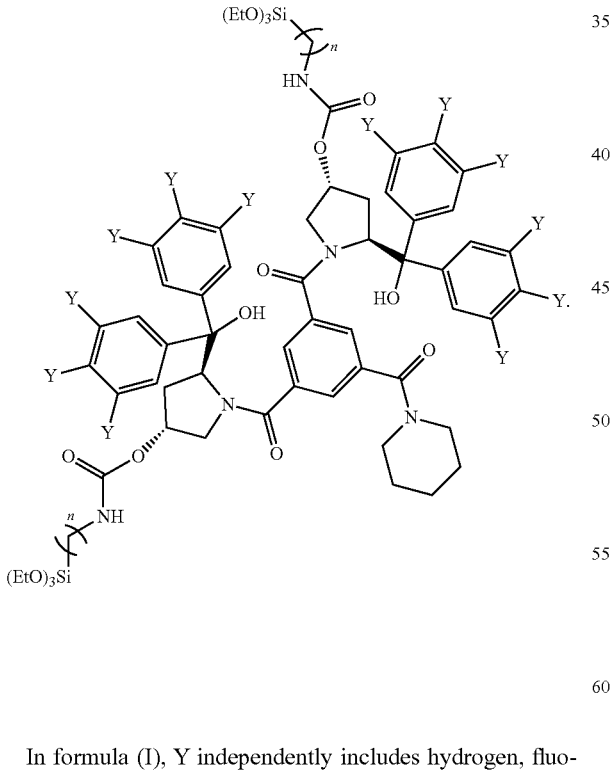

(I)

In formula (I), Y independently includes hydrogen, fluorine, trifluoromethyl, isopropyl, tert-butyl, $C_mH_{2m+1}$ or $OC_mH_{2m+1}$, wherein m=1-10 and n=1-10.

The present disclosure provides a chiral catalyst represented by formula (II):

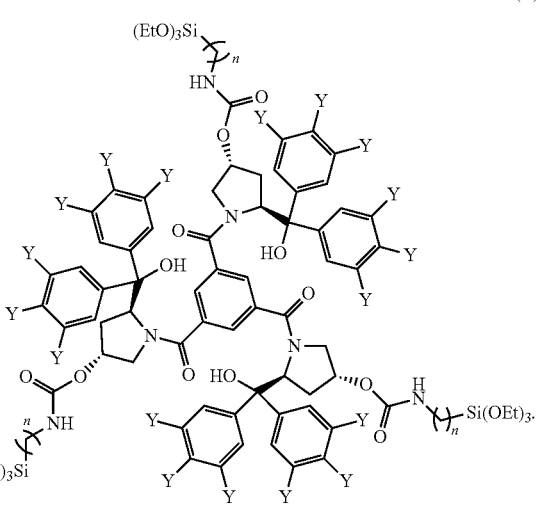

(II)

In formula (II), Y independently includes hydrogen, fluorine, trifluoromethyl, isopropyl, tert-butyl, $C_mH_{2m+1}$ or $OC_mH_{2m+1}$, wherein m=1-10 and n=1-10.

The present disclosure provides a heterogeneous chiral catalyst. The heterogeneous chiral catalyst includes a chiral catalyst represented by formula (II) and a substrate connected to the chiral catalyst.

A detailed description is given in the following embodiments.

DETAILED DESCRIPTION

The present disclosure provides a chiral catalyst represented by formula (I):

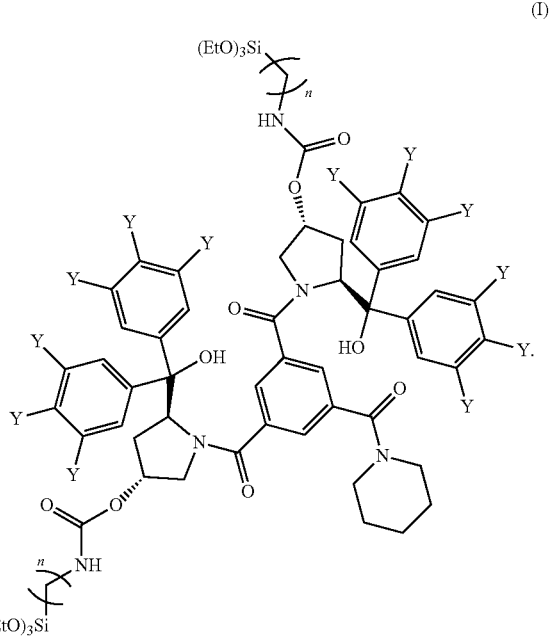

(I)

In formula (I), Y independently includes hydrogen, fluorine, trifluoromethyl, isopropyl, tert-butyl, $C_mH_{2m+1}$ or $OC_mH_{2m+1}$, wherein m=1-10 and n=1-10.

In some embodiments, in formula (I), Y independently includes hydrogen, $CH_3$ or $OCH_3$, and n=3-8.

In some embodiments, the chiral catalyst represented by formula (I) may include the following compound:

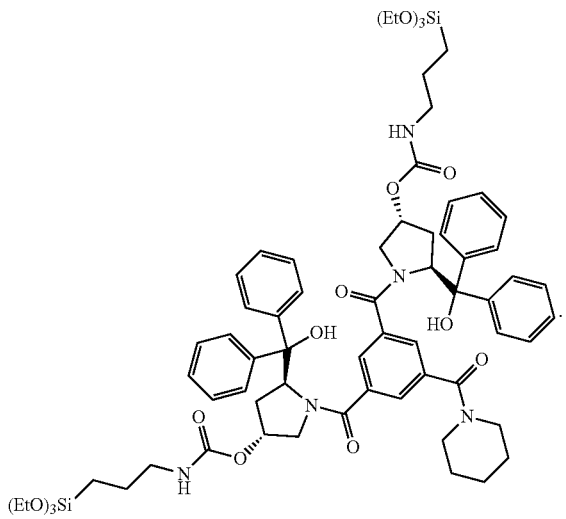

The present disclosure provides a chiral catalyst represented by formula (II):

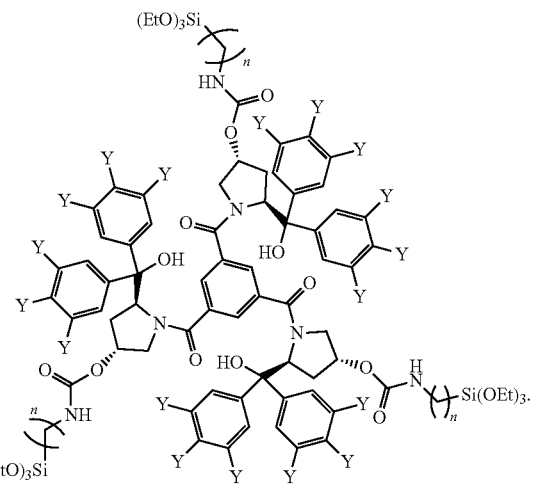

In formula (II), Y independently includes hydrogen, fluorine, trifluoromethyl, isopropyl, tert-butyl, $C_mH_{2m+1}$ or $OC_mH_{2m+1}$, wherein m=1-10 and n=1-10.

In some embodiments, in formula (II), Y independently includes hydrogen, $CH_3$ or $OCH_3$, and n=3-8.

In some embodiments, the chiral catalyst represented by formula (II) may include the following compound:

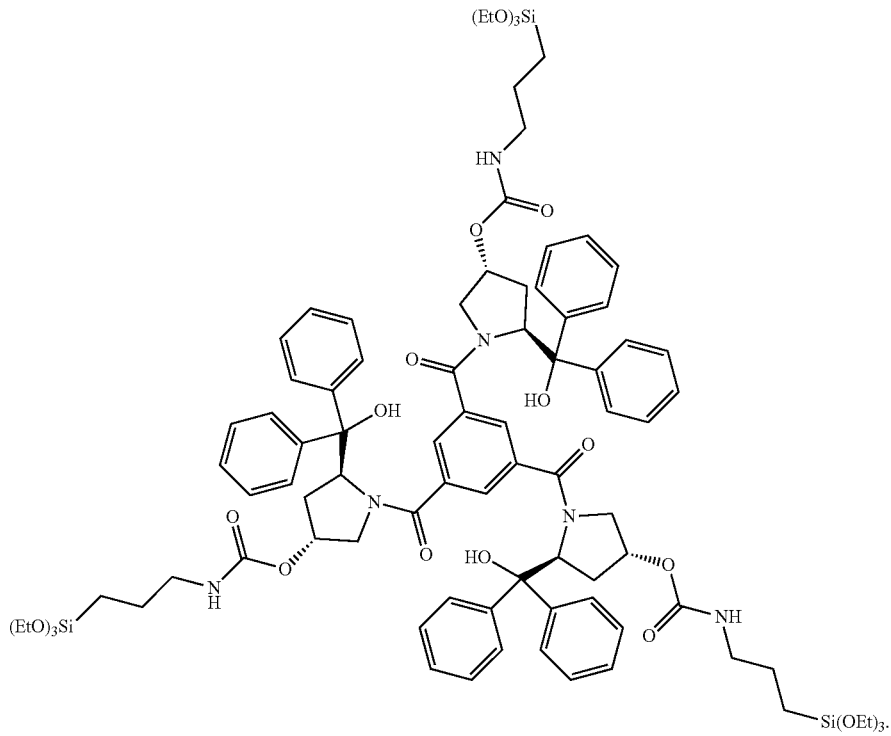

The present disclosure provides a heterogeneous chiral catalyst. The heterogeneous chiral catalyst includes a chiral catalyst and a substrate connected to the chiral catalyst.

In some embodiments, the chiral catalyst is represented by formula (II):

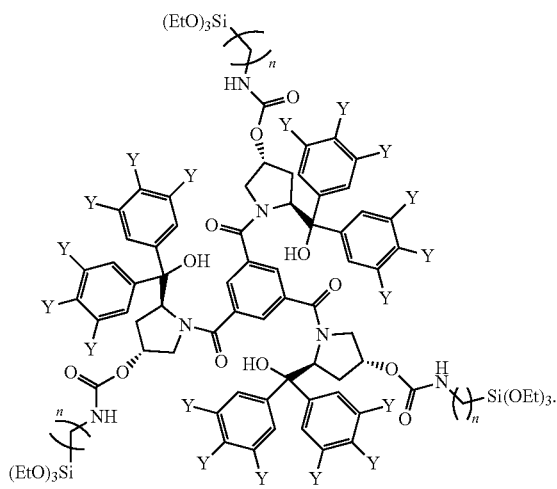

(II)

In formula (II), Y independently includes hydrogen, fluorine, trifluoromethyl, isopropyl, tert-butyl, $C_mH_{2m+1}$ or $OC_mH_{2m+1}$, wherein m=1-10 and n=1-10.

In some embodiments, in formula (II), Y independently includes hydrogen, $CH_3$ or $OCH_3$, and n=3-8.

In some embodiments, the chiral catalyst represented by formula (II) may include the following compound:

In some embodiments, the surface of the substrate may include hydroxyl groups (—OH). In some embodiments, the substrate may include silicon oxide, titanium oxide, iron oxide, zinc oxide or aluminum oxide. In some embodiments, the specific surface area of the substrate is in a range from about 10 $m^2/g$ to about 1,000 $m^2/g$. In some embodiments, the pore size of the substrate is in a range from about 2 nm to about 50 nm. In some embodiments, the hydroxyl group of the substrate is connected to the $Si(OEt)_3$ group of the chiral catalyst. In some embodiments, a silicon-oxygen bond is formed between the substrate and the chiral catalyst.

The present disclosure develops a novel chiral catalyst, which uses the basic structure "(S)-(−)-α,α-Diphenyl-2-pyrrolidinemethanol" of Corey-Bakshi-Shibata (CBS) catalyst to synthesize C3-Symmetric structural molecules. In order to solve the problem of the catalyst recovery from a homogeneous reaction, this chiral catalyst molecule having three side chains with silanization further forms a covalent bond with $SiO_2$ and is fixed on the surface of $SiO_2$. When solvent and ketone compounds (reactants) flow through, the reactants react with the chiral catalyst on $SiO_2$ to generate a force to proceed to a catalytic reaction. After the reaction is complete, the synthesized chiral alcohol compounds are removed with the flow of the solvent, which helps to separate the product from the catalyst, facilitates recycling and reuse, and can improve the reuse rate of the catalyst. The selective reduction method involving this chiral catalyst can effectively increase the optical purity and conversion rate of the product. In addition, the present disclosure can realize continuous reduction reaction and synthesize chiral alcohol compounds in a more economical and efficient manner.

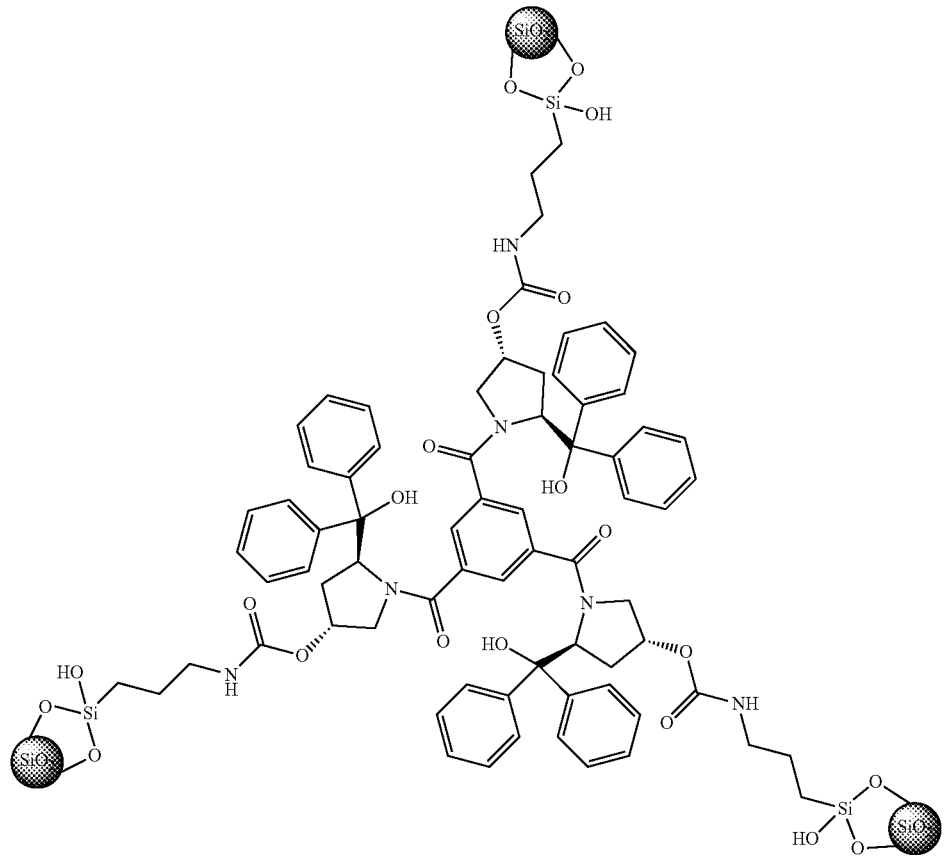

Example 1

Preparation of the Chiral Catalyst

Step 1

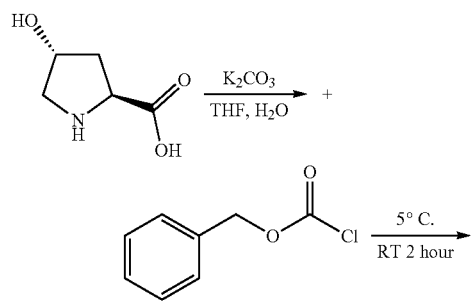

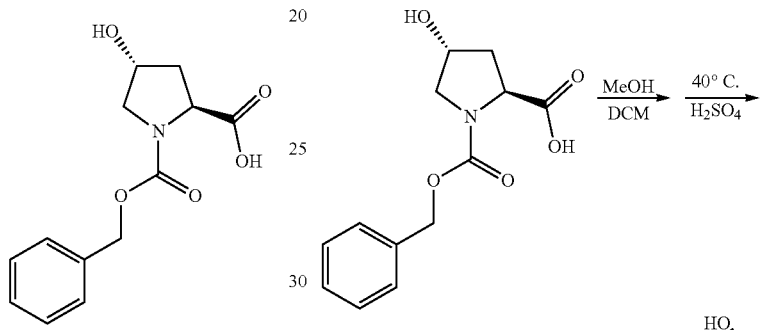

[reagent]

| code | reactant | molecular weight | amount | mmoles | molar ratio |
|------|----------|------------------|--------|--------|-------------|
| R1 | trans-4-Hydroxy-L-proline | 131.13 | 30 g | 228.78 | 1 |
| R2 | Potassium carbonate | 138.21 | 39.52 g | 285.97 | 1.25 |
| R3 | Tetra-hydrofuran/Water | — | 120/160 mL | — | — |
| R4 | Benzyl chloroformate/Tetra-hydrofuran | 170.59 | 35.8/120 mL | 251.66 | 1.1 |

[Synthesis Steps]

First, a 1-L double-necked reaction flask was provided, after being purged with nitrogen, R1-R3 were added to the flask and stirred until completely dissolved. Next, the reaction flask was placed in an ice bath with conduction of nitrogen to cool down, and the temperature in the ice bath was maintained at 0-5° C. Next, R4 solvent was slowly dripped into the reaction flask. After finishing dripping, the temperature of the reaction solution was allowed to return to room temperature with stirring for 2 hours. Next, an HPLC measurement (hexane (Hex):isopropanol (IPA)=4:1 and 0.1% trifluoroacetic acid (TFA)) with flow rate of 0.5 mL/min was performed, and the retention time of the product appeared at 14.92 min [REGIS (S,S) Whelk-O1 5 μm, 4.6×150 mm]. After the reaction was complete, 300 mL of $H_2O$ was added, and extracted with 100 mL of ethanolamine (EA) each time and repeated 4 times (total 400 mL of EA). The EA layer was inspected by HPLC and no product was detected in the EA layer. Next, the aqueous layer was acidified with a 3M HCl aqueous solution to pH=2, and then extracted with 100 mL of EA each time and repeated 4 times (total 400 mL of EA). The EA layer was dehydrated with anhydrous magnesium sulfate and filtered, and then the solvent was removed at 40° C. using a rotary concentrator. Next, a vacuum drying step was performed at room temperature for 12 hours and 54 g of transparent liquid was obtained. The yield was 89.0%, and an HPLC measurement (Hex:IPA=4:1 and 0.1% TFA) with flow rate of 0.5 mL/min was performed, and the product appeared at 14.70 min. The purity thereof was 99.2%. The target product was measured by NMR. Data are as follows: $^1H$ NMR (400 MHz, $DMSOd_6$): δ 12.63 (s, 1H, COOH), 7.36-7.28 (m, 5H), 5.10-5.00 (m, 3H, OH, $PhCH_2O$), 4.30-4.19 (m, 2H), 3.50-3.36 (m, 2H), 2.21-2.11 (m, 1H), 1.99-1.81 (m, 1H).

Step 2

[Reagent]

| code | reactant | molecular weight | amount | mmoles | molar ratio |
|------|----------|------------------|--------|--------|-------------|
| R1 | product of Step 1/Methanol | 265.26 | 54 g/75 mL | 203.57 | 1 |
| R2 | Methanol/Dichloro-methane | — | 50/250 mL | — | — |
| R3 | Sulfuric acid, D = 1.84 | 98.08 | 1.5 mL | 28.11 | 0.15 |
| R4 | Potassium carbonate/Water | 138.21 | 8.4 g/200 mL | 61.07 | 0.3 |

[Synthesis Steps]

First, a 500-mL double-necked reaction flask was provided, after being purged with nitrogen, R1-R3 were added to the flask and stirred until completely dissolved. Next, the reaction flask was placed in an oil bath with conduction of nitrogen to cool down, and the temperature in the oil bath was maintained at 40-50° C. Next, the reaction was tracked by HPLC (Hex:IPA=4:1 and 0.1% TFA) with flow rate of 1.0 mL/min, and the product appeared at 11.53 min [REGIS (S,S) Whelk-O1 5 μm, 4.6×150 mm]. The reaction was complete after 12 hours. After the reaction was complete, the solution was concentrated to 20-30 mL. R4 aqueous solution was added and extracted with 100 mL of EA each time and repeated 3 times (total 300 mL of EA). The EA layer was dehydrated with anhydrous magnesium sulfate and filtered, and then the solvent was removed at 50° C. using a rotary concentrator. Next, a vacuum drying step was performed at room temperature for 12 hours and 57.8 g of light-yellow transparent liquid was obtained. The yield was 79.5%, and an HPLC measurement (Hex:IPA=4:1 and 0.1% TFA) with flow rate of 1.0 mL/min was performed, and the product appeared at 11.51 min. The purity thereof was 98.0%. The target product was measured by NMR. Data are as follows: $^1$H NMR (400 MHz, CDCl$_3$): δ 7.32-7.24 (m, 5H), 5.18-4.96 (m, 2H, PhCH2O), 4.51-4.44 (m, 2H), 3.72-3.59 (m, 0.3H), 3.54-3.52 (m, 2H), 2.32-2.23 (m, 1H), 2.07-1.80 (m, 1H).

Step 3

300 mL of H$_2$O was added and extracted with DCM. The DCM layer was dehydrated with anhydrous magnesium sulfate and filtered, and then the solvent was removed at 40° C. using a rotary concentrator. Next, a vacuum drying step was performed at room temperature for 12 hours and 74.7 g of transparent liquid was obtained. The yield was 99.2%, and an HPLC measurement (Hex:IPA=4:1 and 0.1% TFA) with flow rate of 1.0 mL/min was performed, and the product appeared at 17.52 min. The purity thereof was 99.2%. The target product was measured by NMR. Data are as follows: $^1$H NMR (400 MHz, CDCl$_3$): δ 7.32-7.26 (m, 5H), 5.19-4.98 (m, 2H, PhCH2O), 4.63-4.58 (m, 1H), 4.50-4.37 (m, 2H), 3.83-3.63 (m, 3H+2H), 3.54-3.41 (m, 2H), 2.45-2.29 (m, 1H), 2.14-2.01 (m, 1H), 1.75-1.62 (m, 2H), 1.58-1.39 (m, 4H).

Step 4

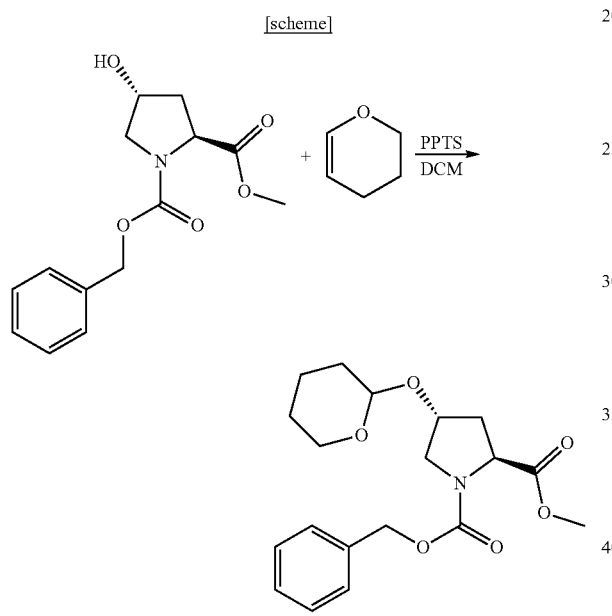

[Reagent]

| code | reactant | molecular weight | amount | mmoles | molar ratio |
|---|---|---|---|---|---|
| R1 | product of Step 2 | 279.29 | 57.9 g | 207.3 | 1 |
| R2 | 3,4-Dihydro-2H-pyran | 84.12 | 26.15 g | 310.97 | 1.5 |
| R3 | Pyridinium p-toluenesulfonate | 251.3 | 0.52 | 2.078 | 0.01 |
| R4 | Dichloromethane | — | 600 mL | — | — |

[Synthesis Steps]

First, a 1-L double-necked reaction flask was provided, after being purged with nitrogen, R1-R4 were added to the flask and stirred until completely dissolved. Next, the reaction flask was placed in an oil bath with conduction of nitrogen to cool down, and the temperature in the oil bath was maintained at 40° C. Next, the reaction was tracked by HPLC (Hex:IPA=4:1 and 0.1% TFA) with flow rate of 1.0 mL/min, and the product appeared at 17.41 min [REGIS (S,S) Whelk-O1 5 μm, 4.6×150 mm]. The reaction was complete after 24 hours. After the reaction was complete,

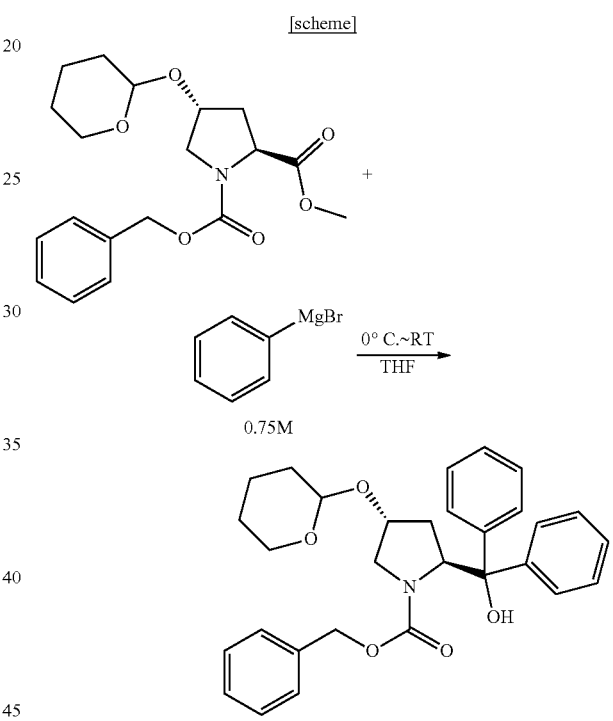

[Reagent]

| code | reactant | molecular weight | amount | mmoles | molar ratio |
|---|---|---|---|---|---|
| R1 | product of Step 3/Tetrahydrofuran | 363.40 | 20 g/200 mL | 55.03 | 1 |
| R2 | Bromobenzene/Tetrahydrofuran | 157.01 | 34.56 g/70 mL | 220.14 | 4 |
| R3 | Magnesium, turnings/Tetrahydrofuran | 24.31 | 5.62 g/10 mL | 231.12 | 4.2 |
| R4 | Tetrahydrofuran, dry | — | 100 mL | — | — |

[Synthesis Steps]

First, a 250-mL double-necked reaction flask was provided, after being purged with nitrogen, R3 was added to the flask and stirred. After about 10-15 mL of R2 was added to the reaction flask dropwise, the reaction was started by heating with a blower and boiled. After R2 was slowly added to the system dropwise, the reaction flask was placed in an oil bath, and the temperature of the oil bath was maintained at 50-60° C. Another 500-mL double-necked reaction flask was provided, purged with nitrogen, and then R1 was added to the flask and stirred to cool down to 0° C. to −5° C. Next, the reaction solution obtained by the above steps was placed in a feeding funnel and slowly dripped into the reaction solution, and the internal temperature was maintained at 0-10° C. After finishing dripping, the solution was heated to 40° C. and reacted for about 2 hours. Next, the reaction was tracked by HPLC (Hex:IPA=4:1 and 0.1% TFA) with flow rate of 1.0 mL/min, and the product appeared at 11.98 min [REGIS (S,S) Whelk-O1 5 μm, 4.6×150 mm]. After the reaction was complete, 3M HCl aqueous solution was added to neutralize to pH=6-8, and extracted with 100 mL of EA each time and repeated 3 times (total 300 mL of EA). The EA layer was dehydrated with anhydrous magnesium sulfate and filtered, and then the solvent was removed at 50° C. using a rotary concentrator. Next, a column (3 cm in diameter) packing 40 cm (SILICYCLE Silica gel 70-230 mesh, pH=7) was provided. After impurities were eluted with EA:Hex=1:10, varied the ratio of EA:Hex to 1:4, and the product was eluted. About 30-50 mL of solvent was removed at 40° C. using a rotary concentrator. Solid was precipitated and filtered. Next, a vacuum drying step was performed at 60° C. for 12 hours, and 16.7 g of white solid was obtained. The yield was 62.3%, and an HPLC measurement (Hex:IPA=4:1 and 0.1% TFA) with flow rate of 1.0 mL/min was performed, and the product appeared at 12.05 min. The purity thereof was 98.5%. The target product was measured by NMR. Data are as follows: $^1$H NMR (400 MHz, CDCl3): δ 7.37-7.24 (m, 15H), 5.10-4.99 (m, 2H, PhCH2O), 4.40-4.36 (d, 1H), 3.71-3.66 (m, 2H+1H), 3.39-3.32 (m, 1H), 2.23-2.09 (m, 2H), 1.70-1.69 (m, 1H), 1.62-1.24 (m, 8H).

Step 5

[Reagent]

| code | reactant | molecular weight | amount | mmoles | molar ratio |
|---|---|---|---|---|---|
| R1 | product of Step 4 | 487.59 | 10 g | 20.51 | 1 |
| R2 | p-Toluene-sulfonic acid | 190.22 | 0.04 g | 0.205 | 0.01 |
| R3 | Ethyl Acetate | — | 50 mL | — | — |
| R4 | Methanol | — | 50 mL | — | — |

[Synthesis Steps]

First, a 250-mL double-necked reaction flask was provided, after being purged with nitrogen, R1-R4 were added to the flask with stirring and heated to an internal temperature of 50-60° C. Next, the reaction was tracked by HPLC (Hex:IPA=4:1 and 0.1% TFA) with flow rate of 1.0 mL/min, and the product appeared at 8.95 min [REGIS (S,S) Whelk-O1 5 μm 4.6×150 mm]. The reaction was complete after about 4 hours. After the reaction was complete, EA was used for extraction. Each extraction was performed with 100 mL of EA and repeated 3 times (total 300 mL of EA). The EA layer was dehydrated with anhydrous magnesium sulfate and filtered, and then the solvent was removed at 50° C. using a rotary concentrator. Next, a vacuum drying step was performed at 60° C. for 12 hours and 8.3 g of white solid was obtained. The yield was 99.0%, and an HPLC measurement (Hex:IPA=4:1 and 0.1% TFA) with flow rate of 1.0 mL/min was performed, and the product appeared at 8.95 min. The purity thereof was 88.0%. Without purification, the next step was performed. The target product was measured by NMR. Data are as follows: $^1$H NMR (400 MHz, CDCl$_3$): δ 7.41-7.27 (m, 15H), 5.18-5.13 (m, 2H, PhCH2O), 4.97 (s, 1H), 3.93 (s, 1H), 3.62-3.59 (d, 1H), 3.08-3.06 (d, 1H), 2.20-1.98 (m, 2H), 1.62-1.60 (m, 2H).

Step 6

[scheme]

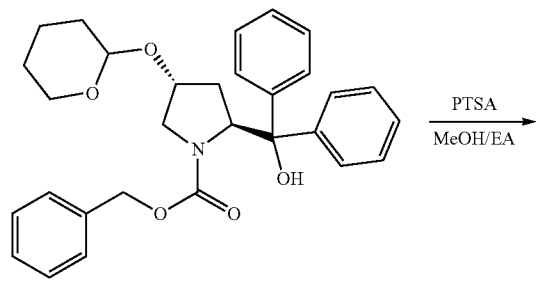

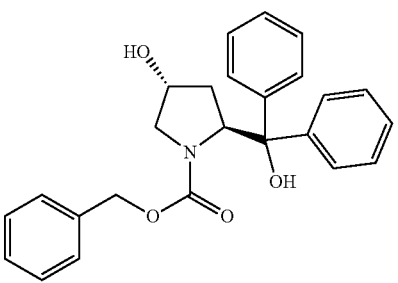

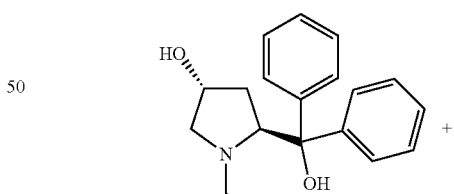

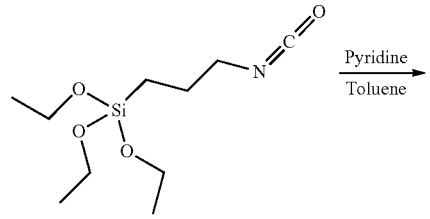

-continued

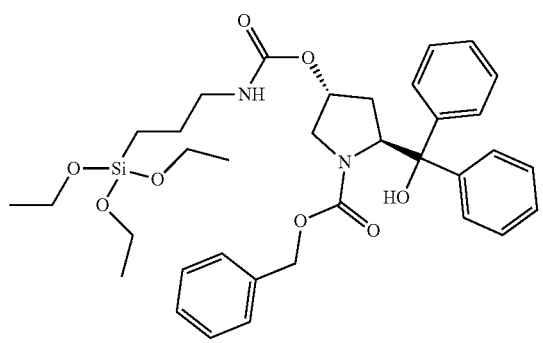

[Reagent]

| code | reactant | molecular weight | amount | mmoles | molar ratio |
|---|---|---|---|---|---|
| R1 | product of Step 5 | 403.47 | 4 g | 9.88 | 1 |
| R2 | 3-(Triethoxysilyl)propyl isocyanate | 247.36 | 4.9 g | 19.76 | 2 |
| R3 | Pyridine | 79.1 | 2.34 g | 29.64 | 3 |
| R4 | Toluene | — | 40 mL | — | — |

[Synthesis Steps]

First, a 100-mL double-necked reaction flask was provided, after being purged with nitrogen, R1-R4 were added to the flask with stirring and heated to thermal reflux. Next, the reaction was tracked by HPLC (Hex:IPA=4:1 and 0.1% TFA) with flow rate of 1.0 mL/min, and the product appeared at 13.24 min [REGIS (S,S) Whelk-O1 5 μm, 4.6×150 mm]. The reaction was complete after about 3 days. After the reaction was complete, EA was used for extraction. Each extraction was performed with 50 mL of EA and repeated 3 times (total 150 mL of EA). The EA layer was dehydrated with anhydrous magnesium sulfate and filtered, and then the solvent was removed at 50° C. using a rotary concentrator. Next, a column (3 cm in diameter) packing 40 cm (SILICYCLE Silica gel 70-230 mesh, pH=7) was provided. After impurities were eluted with EA:Hex=1:10, varied the ratio of EA:Hex to 1:4, and the product was eluted. About 30-50 mL of solvent was removed at 40° C. using a rotary concentrator. Solid was precipitated and filtered. Next, a vacuum drying step was performed at room temperature for 12 hours, and 2.75 g of transparent liquid was obtained. The yield was 45.5%, and an HPLC measurement (Hex:IPA=4:1 and 0.1% TFA) with flow rate of 1.0 mL/min was performed, and the product appeared at 13.2 min. The purity thereof was 94.2%. The target product was measured by NMR. Data are as follows: $^1$H NMR (400 MHz, CDCl3): δ 7.39-7.18 (m, 15H), 5.11-5.03 (m, 2H, PhCH2O), 4.87-4.85 (m, 2H), 4.12-4.07 (m, 1H), 3.81-3.78 (m, 6H), 3.71-3.64 (m, 1H), 3.11-3.05 (m, 2H), 2.25-2.10 (m, 2H), 1.60-1.52 (m, 2H), 1.25-1.16 (m, 9H), 0.61-0.51 (m, 2H).

Step 7

[scheme]

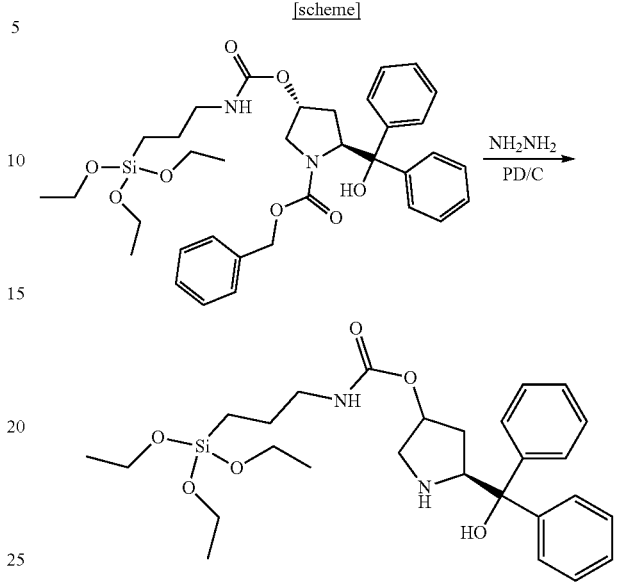

[Reagent]

| code | reactant | molecular weight | amount | mmoles | molar ratio |
|---|---|---|---|---|---|
| R1 | product of Step 6 | 650.83 | 2 g | 3.06 | 1 |
| R2 | Palladium on carbon 5% | — | 0.2 g | — | — |
| R3 | Hydrazine monohydrate | 50.06 | 0.23 g | 4.6 | 1.5 |
| R4 | Methanol | — | 20 mL | — | — |

[Synthesis Steps]

First, a 100-mL double-necked reaction flask was provided, purged with nitrogen, and then R1-R4 were added to the flask with stirring and heated to an internal temperature of 50-60° C. Next, the reaction was tracked by HPLC (Hex:IPA=4:1 and 0.1% TFA) with flow rate of 1.0 mL/min, and the product appeared at 4.79 min [REGIS (S,S) Whelk-O1 5 μm, 4.6×150 mm]. The reaction was complete after about 3 hours. Next, the solvent was removed at 50° C. using a rotary concentrator. Next, a column (3 cm in diameter) packing 20 cm (SILICYCLE Silica gel 70-230 mesh·pH=7) was provided using an eluent (EA:Hex=1:6). After impurities were washed out, the eluent (EA:Hex=1:1) was used to elute the product. The product was then concentrated and dried. After a vacuum drying step was performed at room temperature for 12 hours, 0.6 g of transparent liquid was obtained. The yield was 38.0%, and an HPLC measurement (Hex:IPA=4:1 and 0.1% TFA) with flow rate of 0.5 mL/min was performed, and the product appeared at 10.2 min. The purity thereof was 93.0%. The target product was measured by NMR. Data are as follows: $^1$H NMR (400 MHz, CDCl3): δ 7.58-7.53 (m, 2H), 7.44-7.42 (m, 2H), 7.30-7.11 (m, 6H), 5.06 (s, 1H), 4.90 (s, 1H), 4.51-4.47 (m, 1H), 3.82-3.77 (m, 6H), 3.26-3.22 (m, 2H), 3.15-3.04 (m, 2H), 1.63-1.51 (m, 4H), 1.22-1.19 (m, 9H), 0.62-0.58 (m, 2H).

Step 8

[scheme]

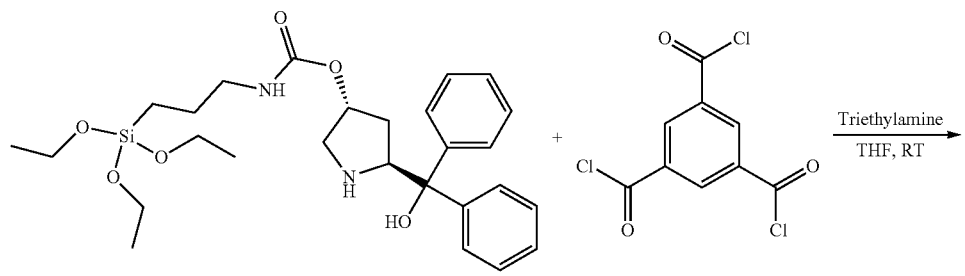

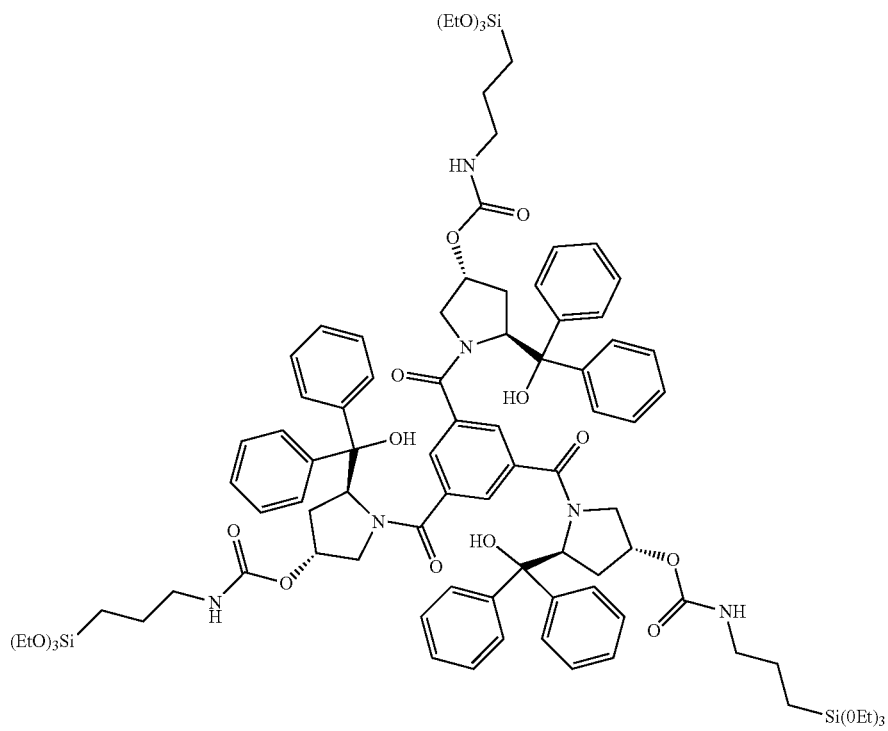

[Reagent]

| code | reactant | molecular weight | amount | mmoles | molar ratio |
|---|---|---|---|---|---|
| R1 | product of Step 7 | 516.70 | 0.53 g | 1.025 | 3.3 |
| R2 | 1,3,5-Benzenetricarbonyl Trichloride, D = 1.487 | 265.47 | 0.082 g | 0.310 | 1 |
| R3 | Tetrahydrofuran | — | 20 mL | — | — |
| R4 | Triethylamine, D = 0.726 | 101.19 | 0.93 g/1.3 mL | 9.225 | 9 |

[Synthesis Steps]

First, a 100-mL double-necked reaction flask was provided, purged with nitrogen, and then R1-R3 were added to the flask with stirring. After R4 was slowly dripped into the above reaction solution, solid salts were precipitated. The reaction was complete after about 24 hours. After the reaction was complete, EA was used for extraction. Each extraction was performed with 100 mL of EA and repeated 3 times (total 300 mL of EA). The EA layer was dehydrated with anhydrous magnesium sulfate and filtered, and then the solvent was removed at 35° C. using a rotary concentrator. The filtrate was dissolved in 10 mL of acetone and recrystallized using hexane. The product was filtered using the FP-450 filter paper (Life Sciences). Next, a vacuum drying step was performed at 40° C. for 12 hours, and 0.4 g of white solid was obtained. The yield was 77.6%, and an HPLC measurement (Hex:IPA=4:1 and 0.1% TFA) with flow rate of 0.5 mL/min was performed, and the product appeared at 5.43 min [REGIS (S,S) Whelk-O1 5 μm, 4.6×150 mm]. The purity thereof was 98.9%. The target product was measured by NMR. Data are as follows: $^1$H NMR (400 MHz, CDCl$_3$): δ 7.59-7.52 (m, 6H), 7.45-7.41 (m, 6H), 7.35-6.99 (m, 27H+3H), 5.05 (s, 3H), 4.94 (s, 3H), 4.50-4.45 (m, 3H), 3.80-3.75 (m, 18H), 3.27-3.30 (m, 6H), 3.18-2.93 (m, 6H), 1.64-1.51 (m, 12H), 1.23-1.18 (m, 27H), 0.60-0.57 (m, 6H). The target product was measured by mass spectrometry. Data are as follow: HRESI: Impact HD Q-TOF mass spectrometer (Bruker, Germany), calcd for $C_{90}H_{120}N_6O_{21}Si_3$=1705.78, found $[M+Na]^+$=1728.75, Na=22.98.

Step 9

[scheme]

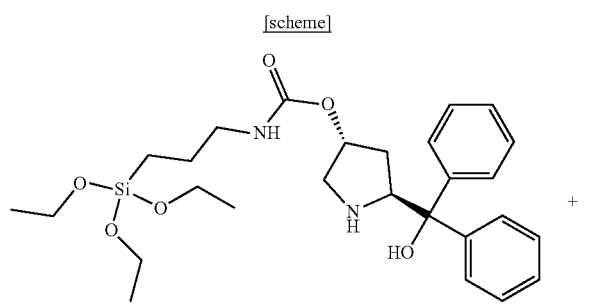

+

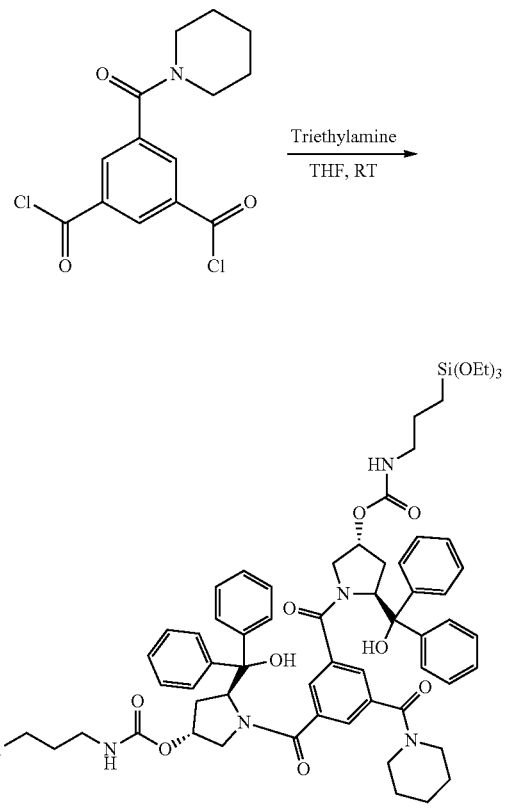

[Reagent]

| code | reactant | molecular weight | amount | mmoles | molar ratio |
|------|----------|------------------|--------|--------|-------------|
| R1 | product of Step 7 | 516.70 | 0.516 g | 1.0 | 2.2 |
| R2 | 1-piperidinyl-carbonyl-3,5-Benzenedicarbonyl dichloride | 314.16 | 0.143 g | 0.455 | 1 |
| R3 | Tetrahydrofuran | — | 20 mL | — | — |
| R4 | Triethylamine, D = 0.726 | 101.19 | 0.42 g/0.57 mL | 4.1 | 9 |

[Synthesis Steps]

First, a 100-mL double-necked reaction flask was provided, purged with nitrogen, and then R1-R3 were added to the flask with stirring. After R4 was slowly dripped, solid salts were precipitated. The reaction was complete after about 24 hours. After the reaction was complete, EA was used for extraction. Each extraction was performed with 100 mL of EA and repeated 3 times (total 300 mL of EA). The EA layer was dehydrated with anhydrous magnesium sulfate and filtered, and then the solvent was removed at 35° C. using a rotary concentrator. The filtrate was dissolved in 10 mL of acetone and recrystallized using hexane. The product was filtered using the FP-450 filter paper (Life Sciences). Next, a vacuuming step was performed at 40° C. for 12 hours, and 0.46 g of gray solid was obtained. The yield was 80.1%, and an HPLC measurement (Hex:IPA=4:1 and 0.1% TFA) with flow rate of 0.5 mL/min was performed, and the product appeared at 6.46 min [REGIS (S,S) Whelk-O1 5 μm, 4.6×150 mm]. The purity thereof was 98.6%. The target product was measured by NMR. Data are as follows: $^1$H NMR (400 MHz, CDCl$_3$): δδ 7.58-7.51 (m, 4H), 7.44-7.38 (m, 4H), 7.38-7.02 (m, 18H+3H), 5.11 (s, 2H), 4.98 (s, 2H), 4.51-4.46 (m, 2H), 3.81-3.72 (m, 12H), 3.38-3.42 (m, 4H), 3.26-3.31 (m, 4H), 3.20-2.94 (m, 4H), 1.69-1.50 (m, 8H+6H), 1.23-1.16 (m, 18H), 0.61-0.56 (m, 4H).

Example 2
Preparation of the Heterogeneous Chiral Catalyst
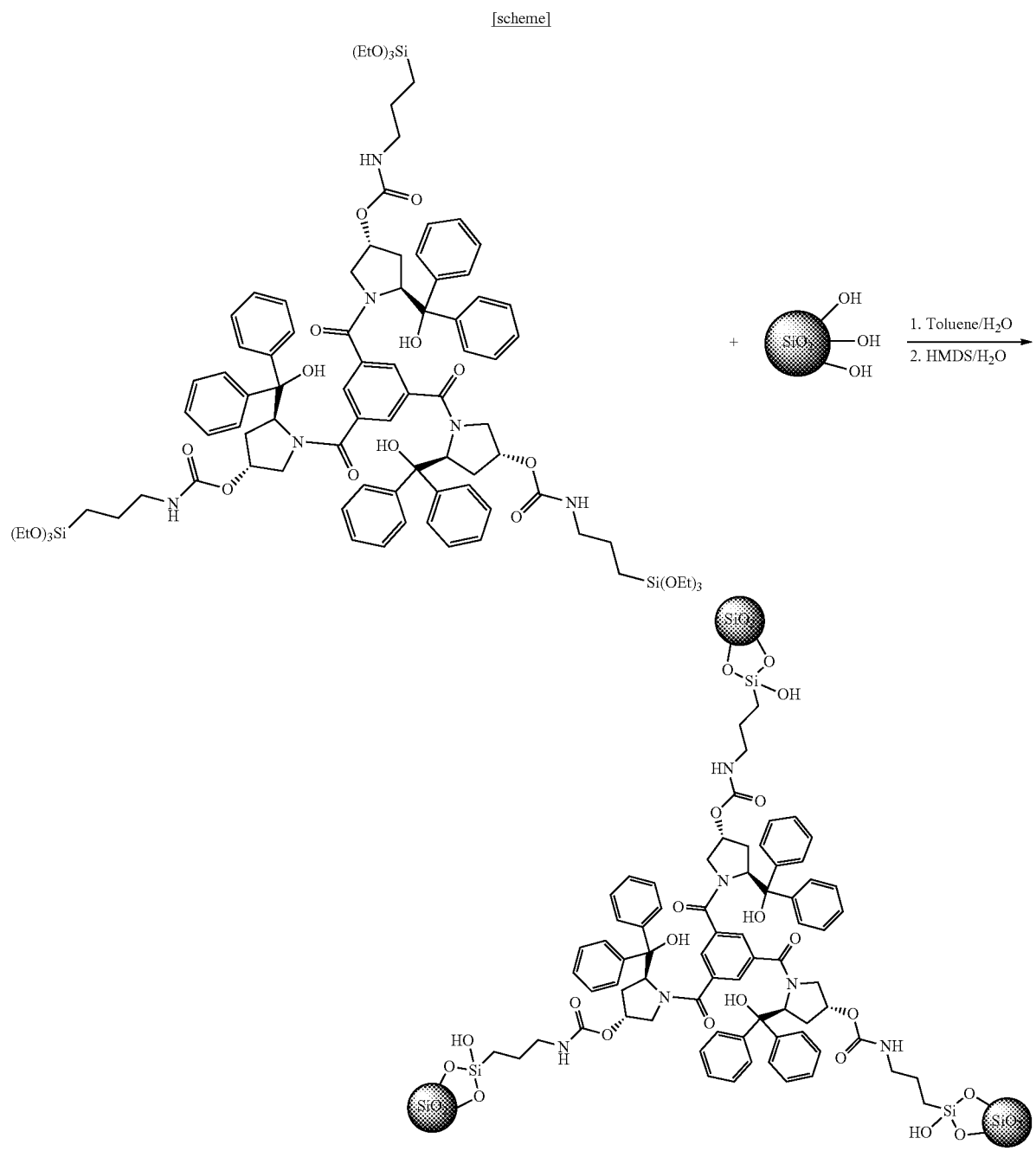
[Reagent]
| code | reactant | molecular weight | amount | mmoles | molar ratio |
|---|---|---|---|---|---|
| R1 | product of Step 8 | 1705.78 | 0.6 g | — | 1 |
-continued
| code | reactant | molecular weight | amount | mmoles | molar ratio |
|---|---|---|---|---|---|
| R2 | $SiO_2$ (G60 or SBA-15) | — | 1.8 g | — | 3 |
| R3 | Toluene | — | 24 mL | — | — |
| R4 | DI Water | — | 2.4 μL | — | — |

| code | reactant | molecular weight | amount | mmoles | molar ratio |
|---|---|---|---|---|---|
| R5 | Toluene | — | 24 mL | — | — |
| R6 | DI Water | — | 2.4 μL | — | — |
| R7 | Hexamethyl-disilazane (HMDS) | 161.40 | 2.4 g | | 4 |

[Synthesis Steps]

First, a 100-mL double-necked reaction flask was provided, purged with nitrogen, and then R1-R4 were added to the flask with stirring and heated to 80° C. The reaction was complete after about 24 hours. The product was filtered using the FP-450 filter paper (Life Sciences). The solids were washed using a continuous extraction apparatus. The solvents used were methanol, acetone and dichloromethane. After cleaning, the product was filtered using the FP-450 filter paper (Life Sciences). A vacuum drying step was performed at 40° C. for 12 hours, and gray solids of 2.28 g of G60 and 2.13 g of SBA-15 were obtained. A 100-mL double-necked reaction flask was provided, purged with nitrogen, and the product obtained from the above step and R5-R7 were added to the flask with stirring and heated to 80° C. The reaction was complete after about 24 hours. The product was filtered using the FP-450 filter paper (Life Sciences). The solids were washed using a continuous extraction apparatus. The solvents used were methanol, acetone and dichloromethane. After washing, the product was filtered using the FP-450 filter paper (Life Sciences). A vacuum drying step was performed at 40° C. for 12 hours, and gray solids of 2.20 g of G60 and 2.11 g of SBA-15 were obtained. The target product was then measured by IR.

G60 [catalyst (IV)]: —CH2 (2928 nm, 2854 nm, 1456 nm), —CONH (1645 nm), 3°-OH (1180-1250 nm), -Ph (702-754 nm).

SBA-15 [catalyst (V)]: —CH2 (2927 nm, 2857 nm, 1449 nm), —CONH (1643 nm), 3°-OH (1162-1245 nm), -Ph (702-753 nm).

Example 3

Chiral Catalysts for Selective Reduction Reaction

[scheme]

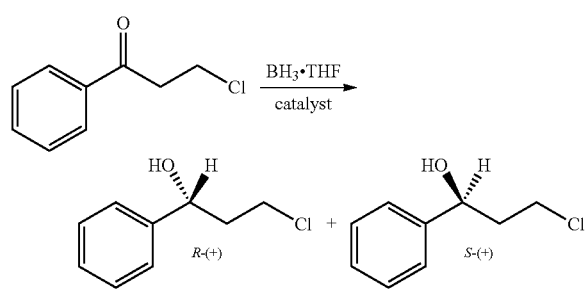

In this example, Catalysts (I), (II) and (III) were provided to perform the selective reduction reaction.

Catalyst (I):

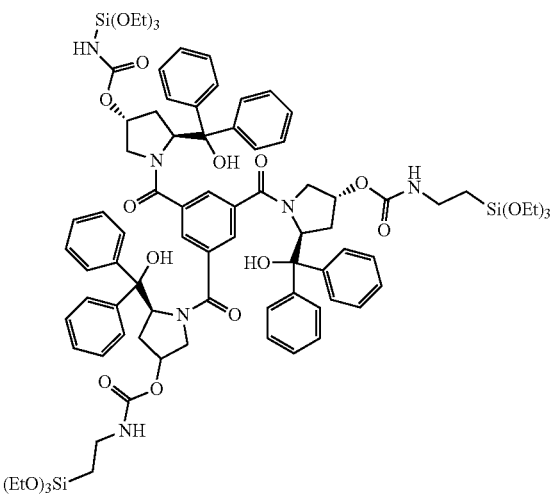

Catalyst (II):

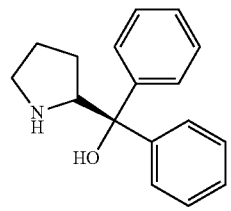

Catalyst (III):

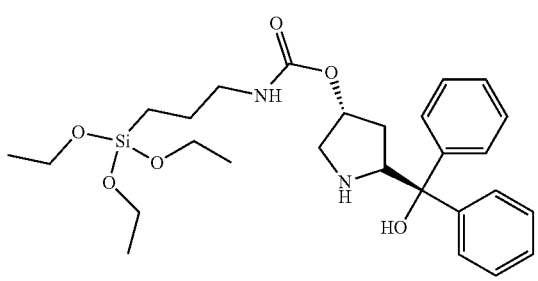

After the reaction was complete, the optical purity and conversion rate of the product were calculated. The results are shown in Table 1. The optical purity (ee) was calculated as follows:

$$\text{Enantiomeric excess } (\%\ ee) = \frac{[R] - [S]}{[R] + [S]}$$

TABLE 1

| catalyst | % mol | R-(+) | S-(−) | ketone | ee | R-(+) conversion rate |
|---|---|---|---|---|---|---|
| (I) | 10% | 87.9% | 12.1% | 0% | 75.7% | 87.9% |
| (II) | 10% | 85.0% | 15.0% | 0% | 69.9% | 85.0% |
| (III) | 10% | 84.7% | 15.3% | 0% | 69.4% | 84.7% |

From the results in Table 1, it can be seen that, in the selective reduction reaction added with the present catalyst (I) having three silane-containing side chains, both the optical purity and conversion rate of the product were higher than those of the product in the selective reduction reaction added with the catalysts (II) and (III).

Example 4

Heterogeneous Chiral Catalysts for Selective Reduction Reaction

[scheme]

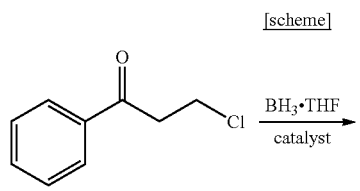

-continued

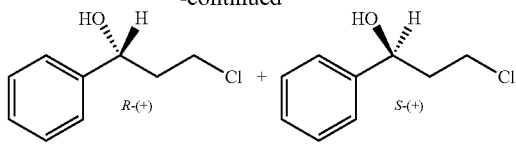

In this example, Catalysts (IV) and (V) were provided to perform the selective reduction reaction.

Catalyst (IV):

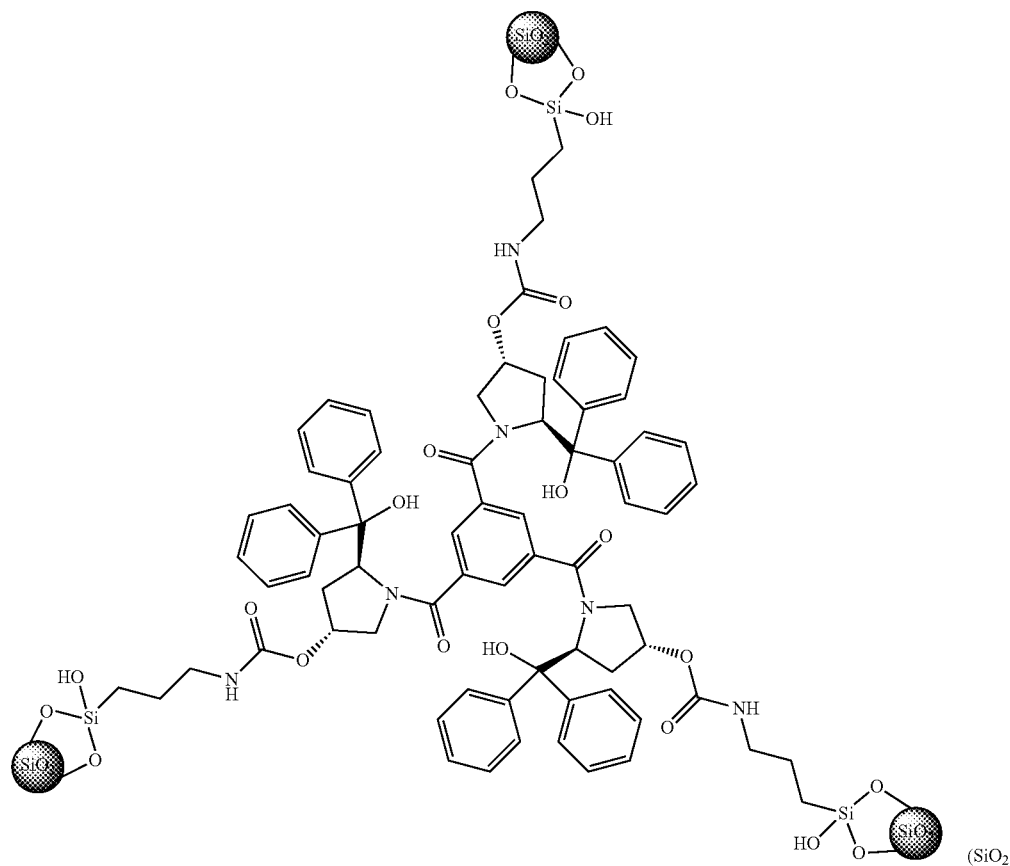

particle size: 63-200 μm: pH=7)

Catalyst (V):

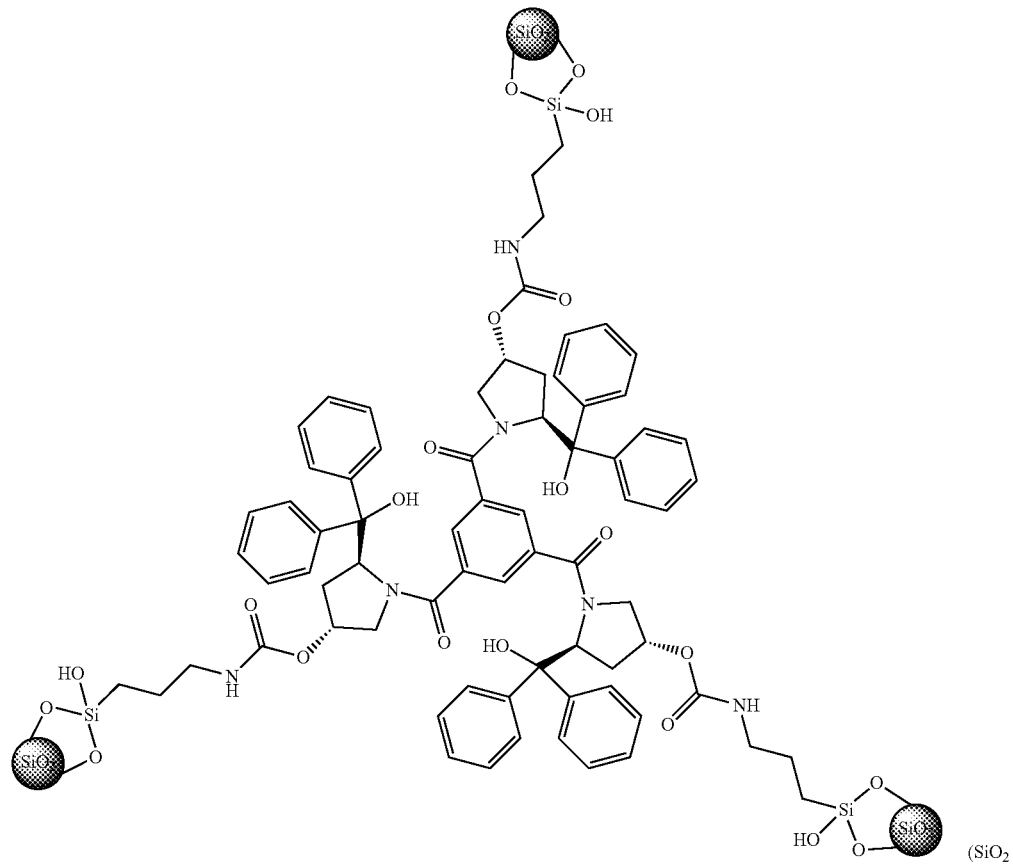

specific surface area: 750 m²/g: particle size: less than 150 μm; pore size: 6 nm: pore capacity: 0.5-0.7 cm³/g)

After the reaction was complete, the optical purity and conversion rate of the product were calculated. The results are shown in Table 2.

| Catalyst | R-(+) | S-(−) | ketone | ee | R-(+) conversion |
|---|---|---|---|---|---|
| (IV) | 83.0% | 16.1% | 0.9% | 67.5% | 83.0% |
| (V) | 88.3% | 11.4% | 0.3% | 77.2% | 88.3% |

From the results in Table 2, it can be seen that, in the selective reduction reaction added with the present heterogeneous chiral catalyst connected to the substrate (for example, silicon dioxide), both the optical purity and conversion rate of the product can achieve good results. Even the optical purity of the product can reach 77.2%, and the conversion rate thereof can reach 88.3%.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A chiral catalyst, represented by formula (I):

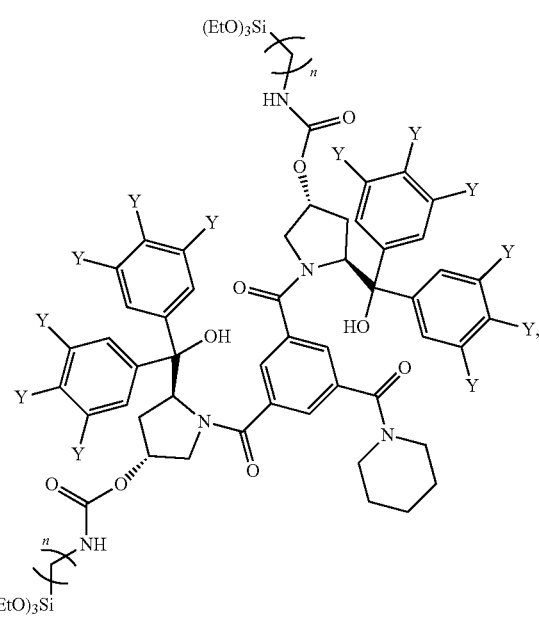

(I)

wherein Y independently comprises hydrogen, fluorine, trifluoromethyl, isopropyl, tert-butyl, $C_mH_{2m+1}$ or $OC_mH_{2m+1}$, wherein m=1-10 and n=1-10.

2. The chiral catalyst as claimed in claim 1, wherein Y independently comprises hydrogen, $CH_3$ or $OCH_3$, and n=3-8.

3. The chiral catalyst as claimed in claim 1, wherein the chiral catalyst comprises:

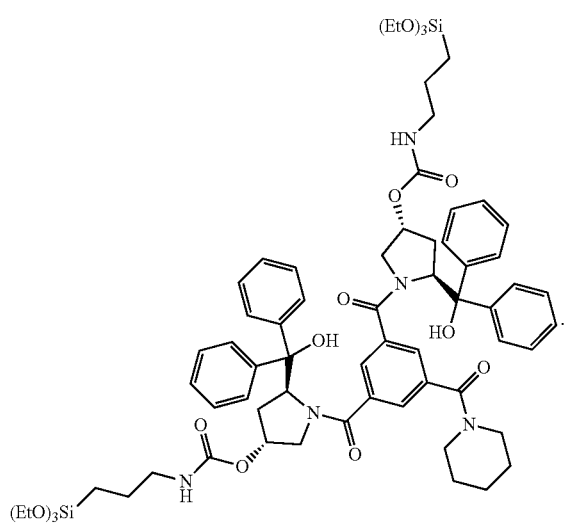

4. A chiral catalyst, represented by formula (II):

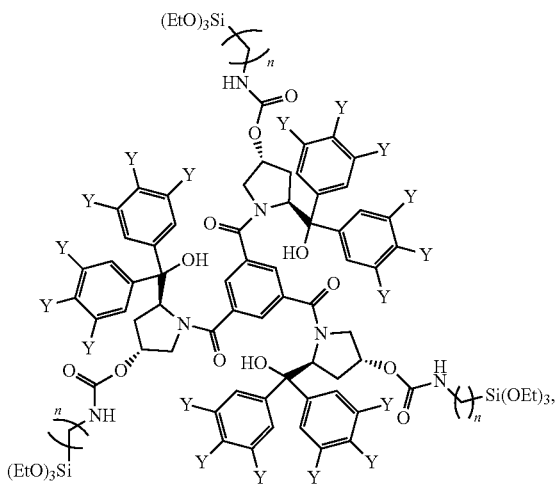

(II)

wherein Y independently comprises hydrogen, fluorine, trifluoromethyl, isopropyl, tert-butyl, $C_mH_{2m+1}$ or $OC_mH_{2m+1}$, wherein m=1-10 and n=1-10.

5. The chiral catalyst as claimed in claim 4, wherein Y independently comprises hydrogen, $CH_3$ or $OCH_3$, and n=3-8.

6. The chiral catalyst as claimed in claim 4, wherein the chiral catalyst comprises:

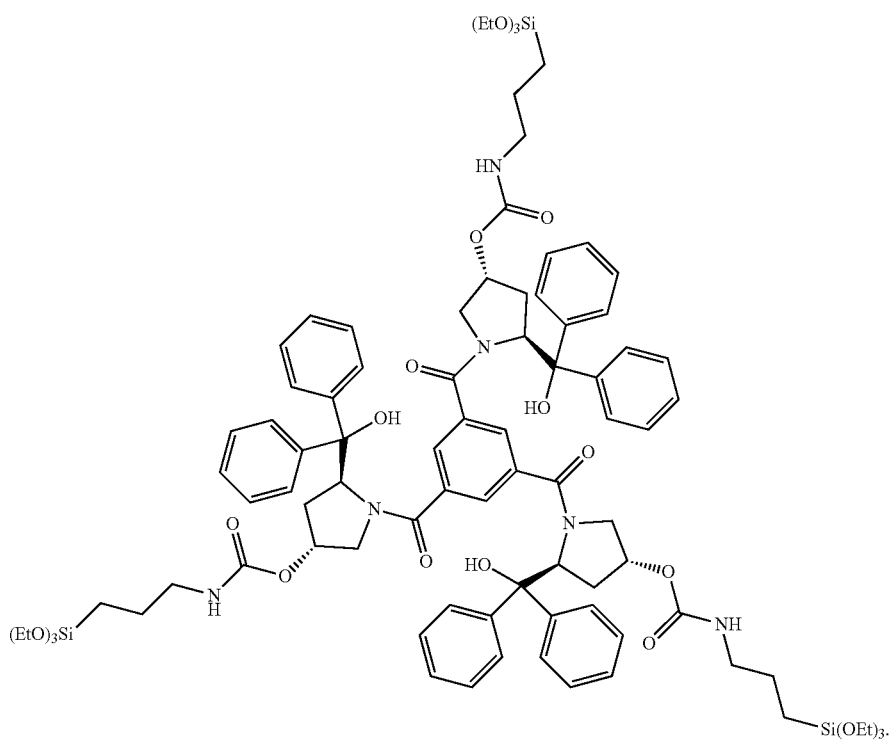

7. A heterogeneous chiral catalyst, comprising:
a chiral catalyst as claimed in claim 4; and
a substrate connected to the chiral catalyst.

8. The heterogeneous chiral catalyst as claimed in claim 7, wherein the surface of the substrate comprises hydroxyl groups.

9. The heterogeneous chiral catalyst as claimed in claim 8, wherein the substrate comprises silicon oxide, titanium oxide, iron oxide, zinc oxide or aluminum oxide.

10. The heterogeneous chiral catalyst as claimed in claim 9, wherein the substrate has a specific surface area which is in a range from 10 m$^2$/g to 1,000 m$^2$/g.

11. The heterogeneous chiral catalyst as claimed in claim 9, wherein the substrate has a pore size which is in a range from 2 nm to 50 nm.

12. The heterogeneous chiral catalyst as claimed in claim 8, wherein the hydroxyl group of the substrate is connected to the Si(OEt)$_3$ group of the chiral catalyst.

13. The heterogeneous chiral catalyst as claimed in claim 12, wherein a silicon-oxygen bond is formed between the substrate and the chiral catalyst.

* * * * *